United States Patent [19]

Son et al.

[11] 4,073,770

[45] Feb. 14, 1978

[54] SUBSTITUTED DECAHYDROQUINOLINES AND THEIR USE AS ULTRAVIOLET LIGHT STABILIZERS

[75] Inventors: Pyong-Nae Son, Akron; Robert Wesley Layer, Cuyahoga Falls, both of Ohio

[73] Assignee: The B. F. Goodrich Company, Akron, Ohio

[21] Appl. No.: 697,345

[22] Filed: June 18, 1976

[51] Int. Cl.$^2$ ............................................. C08J 3/20
[52] U.S. Cl. .................... 260/45.8 NW; 260/45.95 P; 260/283 R; 260/800; 260/814
[58] Field of Search ............... 260/45.8 NW, 45.95 P, 260/283 R, 800, 814

[56] References Cited

U.S. PATENT DOCUMENTS

| | | | |
|---|---|---|---|
| 2,500,229 | 3/1950 | Arnold et al. | 260/45.8 NW |
| 2,500,597 | 3/1950 | Arnold et al. | 260/45.8 NW |
| 2,831,861 | 4/1958 | Wilde | 260/800 |
| 2,832,749 | 4/1958 | Harris | 260/45.8 NW |
| 2,998,468 | 8/1961 | Wilde | 260/800 |
| 3,083,181 | 3/1963 | Harris | 260/45.8 NW |
| 3,296,189 | 1/1967 | Eastman | 260/45.8 NW |
| 3,362,929 | 1/1968 | Kehe | 260/45.8 NW |
| 3,362,930 | 1/1968 | Kehe | 260/45.8 NW |
| 3,637,745 | 1/1972 | Heller et al. | 260/45.8 NW |
| 3,901,849 | 8/1975 | Dodson et al. | 260/45.8 NW |

*Primary Examiner*—Eugene C. Rzucidlo
*Attorney, Agent, or Firm*—Alan A. Csontos

[57] ABSTRACT

Novel substituted decahydroquinolines are prepared and used as ultraviolet (UV) light stabilizers for materials subject to UV light degradation, particularly for polyolefins. Compositions containing the decahydroquinoline compounds exhibit excellent stability to UV light.

11 Claims, No Drawings

SUBSTITUTED DECAHYDROQUINOLINES AND THEIR USE AS ULTRAVIOLET LIGHT STABILIZERS

BACKGROUND OF THE INVENTION

Materials and products made therefrom must exhibit resistance to degradation if they are to be successfully marketed. Degradation can be seen as a partial or total loss of structural integrity, a darkening or discoloration of the product, a loss of flexibility or resilience, or a combination of the above phenomena. These phenomena are promoted or catalyzed by air (oxygen), heat, and light, particularly ultraviolet light.

To protect materials, ingredients which can be collectively called stabilizers are admixed with the materials to prevent or inhibit degradation. These stabilizers work in diverse and complex ways, such that a compound which stabilizes against heat and oxygen degradation in a material may not stabilize against light degradation in the same material, or vice versa. Furthermore, a compound which acts as a stabilizer against oxygen degradation in one type of material may be relatively inactive in another type of material. Thus, compounds which are stabilizers are further classed as antioxidants, antiozonants, heat stabilizers, and ultraviolet (UV) light stabilizers, depending upon what type of activity and stabilization they demonstrate. In many cases, to obtain optimum protection, a mixture of compounds, each specifically selected to afford maximum protection against a certain type of degradation, is often used.

The present invention is directed to a new class of UV stabilizers. The basic structure of this class is a nitrogen-substituted decahydroquinoline, exemplified in its simplest form as 1,2,2,4-tetramethyldecahydroquinoline. Other art in this area is as follows: U.S. Pat. Nos. 3,362,929; 3,362,930; 3,829,292; 3,901,849; 3,910,918; 3,939,164; Published Patent Application Nos. B402,162 and B571,638; British Patent No. 999,806; and an article in the J. Amer. Chem. Soc., Vol. 60 (1938) at page 1458 et seq.

SUMMARY OF THE INVENTION

The invention is directed to a new class of ultraviolet (UV) light stabilizers having the structural formula

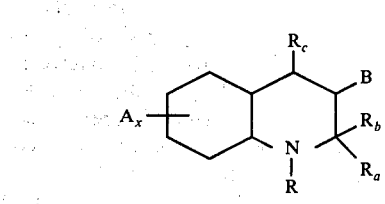

wherein R is selected from the group consisting of alkyl groups containing 1 to about 4 carbon atoms, aralkyl groups of 7 to about 14 carbon atoms, cyclohexylalkyl groups of 7 to 14 carbon atoms total, hydroxyalkyl groups containing 1 to about 12 carbon atoms, haloalkyl groups containing 1 to about 12 carbon atoms, cyanoalkyl groups containing 2 to about 12 carbon atoms, aminoalkyl or iminoalkyl groups containing 2 to about 12 carbon atoms, ether groups containing 3 to about 18 carbon atoms total in the group, hydroxyalkyl or cyanoalkyl ether groups containing 4 to about 18 carbon atoms total in the group, and the group

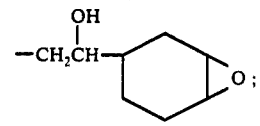

$R_a$, $R_b$, and $R_c$ are each individually alkyl groups containing 1 to about 12 carbon atoms, cyclohexyl groups, or cyclohexylalkyl groups containing 7 to about 14 carbon atoms; A is selected from the group consisting of alkyl groups containing 1 to about 24 carbon atoms, hydroxyalkyl groups containing 1 to about 12 carbon atoms, alkoxy groups containing 1 to about 12 carbon atoms, ester groups containing a total of from 2 to about 24 carbon atoms in the group, cyclohexyl groups, cyclohexylalkyl groups containing 7 to about 14 carbon atoms, hydroxy groups, and amino groups and aminoalkyl groups and alkyl-substituted amino and aminoalkyl groups wherein the alkyl contains 1 to about 12 carbon atoms; x is 0, 1, 2, or 3; and B is hydrogen, an alkyl group containing 1 to about 12 carbon atoms, a cyclohexyl group, or a cyclohexylalkyl group of 7 to about 14 carbon atoms.

Dimers of the above compounds can be prepared and are also part of the claimed invention. The dimer compounds are essentially two decahydroquinoline compounds of the above structural formula attached to each other at the 4-positions, the 6-positions, the 8-positions, the 4'-, 6-positions, and the 4'-, 8-positions on the molecules. An example of a dimer compound of the invention, in its simplest form, is 6-[4'-(1,2,2,4-tetramethyldecahydroquinolyl)]-1,2,2,4-tetramethyldecahydroquinoline.

Furthermore, bis compounds can be prepared and are also part of the claimed invention. The bis compounds are essentially two decahydroquinoline compounds of the above structural formula attached to each other through the 1-positions, the 4-positions, the 6-positions, or the 8-positions via a bivalent radical structure selected from the group consisting of a bivalent alkyl structure and the structure $-(CH_2)_y-G-(CH_2)_z-$ wherein G is -O-, -S-, >NH,

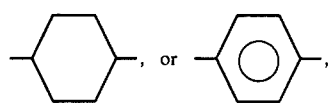

and y and z are individually an integer from 1 to 6. The alkyl can be linear or branched. An example of a bis compound of the invention, in its simplest form, is 6,6'-methylene-bis-(1,2,2,4-tetramethyldecahydroquinoline).

The above compounds are nitrogen-substituted decahydroquinolines. Materials containing these compounds exhibit excellent stability to degradation caused by UV light. The substituted decahydroquinolines are particularly effectual as UV stabilizers for polyolefinic materials such as poly-α-monoolefin homopolymers. The decahydroquinoline compounds of the invention are beneficially used with phenolic antioxidants to provide both excellent UV and oxidative stability to plastic materials.

DETAILED DESCRIPTION

Substituted decahydroquinolines are very efficient and effectual ultraviolet (UV) light stabilizers for the protection of materials subject to UV light degradation. The compounds have the structural formula

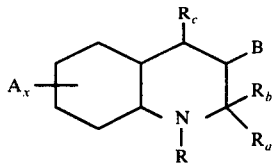

wherein R is selected from the group consisting of alkyl groups containing 1 to about 24 carbon atoms, aralkyl groups of 7 to about 14 carbon atoms, cyclohexylalkyl groups of 7 to about 14 carbon atoms total, hydroxyalkyl groups containing 1 to about 12 carbon atoms, haloalkyl groups containing 1 to about 12 carbon atoms, cyanoalkyl groups containing 2 to about 12 carbon atoms, aminoalkyl or iminoalkyl groups containing 2 to about 12 carbon atoms, ether groups containing 3 to about 18 carbon atoms total in the group, hydroxyalkyl or cyanoalkyl ether groups containing 4 to about 18 carbon atoms total in the group, and the group

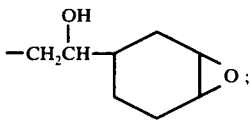

$R_a$, $R_b$, and $R_c$ each independently are alkyl groups containing 1 to about 12 carbon atoms, cyclohexyl groups, or cyclohexylalkyl groups containing 7 to about 14 carbon atoms; A is selected from the group consisting of alkyl groups containing 1 to about 24 carbon atoms, hydroxyalkyl groups containing 1 to about 12 carbon atoms, alkoxy groups containing 1 to about 12 carbon atoms, ester groups containing a total of from 2 to about 24 carbon atoms in the group, cyclohexyl groups, cyclohexylalkyl groups containing 7 to about 14 carbon atoms, hydroxy groups, amino groups and aminoalkyl groups and alkyl-substituted amino and aminoalkyl groups wherein the alkyl contains 1 to about 12 carbon atoms; x is 0, 1, 2, or 3; and B is hydrogen, an alkyl group containing 1 to about 12 carbon atoms, a cyclohexyl group, or a cyclohexylalkyl group of 7 to about 14 carbon atoms.

Illustrative of the type of substituents that can be present on the decahydroquinoline compounds are: for R, when R is alkyl, examples are methyl, ethyl, n-propyl, isopropyl, n-butyl, t-butyl, n-hexyl, n-octyl, 2-ethylhexyl, N-decyl, n-tetradecyl, n-octyldecyl, and the like; when R is aralkyl, examples are benzyl, phenylethyl, and the like; when R is cyclohexylalkyl, examples are cyclohexylmethyl and the like; when R is hydroxyalkyl, examples are 2-hydroxyethyl, 2-hydroxypropyl, 3-hydroxypropyl, 2-hydroxybutyl, 4-hydroxybutyl, 6-hydroxyhexyl, 8-hydroxyoctyl, and the like; when R is haloalkyl, examples are 2-chloroethyl, 2-bromoethyl, 2-fluoroethyl, 2-chlorobutyl, 4-chlorobutyl, 2-β-chloroethylhexyl, and the like; when R is cyanoalkyl, examples are 2-cyanoethyl, 3-cyanopropyl, 4-cyanobutyl, 8-cyanooctyl, and the like; when R is aminoalkyl or iminoalkyl, examples are 2-aminoethyl, 2-aminopropyl, 4-aminobutyl, 6-aminohexyl, α-methyl-2-aminoethyl, and the like; when R is ether, examples are methoxyethyl, ethoxyethyl, ethoxypropyl, octyloxyethyl, phenoxyethyl, p-methylphenoxypropyl, and the like; when R is hydroxyalkyl ether or cyanoalkyl ether, examples are 2-hydroxyethyloxaethyl, p-(2-hydroxypropyl)-phenyloxapropyl, 4-hydroxybutyloxahexyl, 2-cyanoethyloxaethyl, 2-hydroxyethyl-di(oxaethyl), and the like; for $R_a$, $R_b$, or $R_c$, examples are methyl, ethyl, propyl, n-butyl, isobutyl, n-hexyl, 2-ethylhexyl, n-decyl, cyclohexyl, cyclohexylmethyl, 1-cyclohexylethyl, and the like; for A, when A is alkyl, examples are methyl, ethyl, n-propyl, n-butyl, tert-butyl, n-hexyl, 2-ethylhexyl, n-octyl, n-nonyl, n-decyl, n-dodecyl, n-tetradecyl, n-octadecyl, n-eicosyl, and the like; when A is hydroxyalkyl, examples are 2-hydroxyethyl, 2-hydroxypropyl, 3-hydroxypropyl, 4-hydroxybutyl, and the like; when A is alkoxy, examples are methoxy, ethoxy, butyloxy, octyloxy, and the like; when A is ester, examples are methylcarbonyloxyethyl, ethylcarbonyloxyethyl, ethylcarbonyloxypropyl, butylcarbonyloxyhexyl, octylcarbonyloxyhexyl, dodecylcarbonyloxyoctyl, and the like; when A is cyclohexylalkyl, examples are cyclohexylmethyl, 1-cyclohexylethyl, and the like; when A is amino and the like, examples are amino, N-methylamino, N-ethylamino, diethylamino, dioctylamino, aminoethyl, N-methylaminoethyl, and the like; and for B, examples are methyl, ethyl, propyl, n-butyl, n-hexyl, cyclohexyl, cyclohexylmethyl, and the like.

Examples of specific decahydroquinoline compounds are: 1,2,2,4-tetramethyl decahydroquinoline; 1-ethyl-2,2,4-trimethyl decahydroquinoline; 1-decyl-2,2,4-trimethyl decahydroquinoline; 1-decyl-2,4-methyl-2-hexyl decahydroquinoline; 1-butyl-2,4-diethyl-2-isopropyl decahydroquinoline; 1-(2'-hydroxyethyl)-2,2,4-trimethyl decahydroquinoline; 1-(2'-hydroxyethyl)-2,4-diethyl-2-methyl decahydroquinoline; 1-(2'-hydroxypropyl)-2,2,4-trimethyl decahydroquinoline; 1-(2'-hydroxybutyl)-2,2,4-trimethyl decahydroquinoline; 1-(2'-hydroxyethyl)-2-methyl-2,4-dihexyl decahydroquinoline; 1-(4'-cyanobutyl)-2,2-dimethyl-4-butyl decahydroquinoline; 1-(ethoxyethyl)-2,2-diethyl-4-octyl decahydroquinoline 1-(2'-bromoethyl)-2,2-dibutyl-4-methyl decahydroquinoline; 1-(2'-hydroxyethyl)-2,2,4,7-tetramethyl decahydroquinoline; 1-(2'-chloroethyl)-2,2,4-trimethyl decahydroquinoline; 1-hexyl-2,2,4-trimethyl-8-ethyl decahydroquinoline; 1-butyl-2-methyl-2,4-diethyl-6-amino decahydroquinoline; 1-octyl-2,2,4-trimethyl-6-aminoethyl decahydroquinoline; 1-ethyl-2,2-dimethyl-4-cyclohexyl decahydroquinoline; 1-(4'-aminobutyl)-2,4-dimethyl-2-ethyl-8-nonyl decahydroquinoline; 1-(2'-cyanoethyl)-2,2,4-trimethyl decahydroquinoline; 1-octyl-2,4-diethyl-2-methyl-6,8-diethyl decahydroquinoline; 1-(2'-fluoroethyl)-2,2,4-trimethyl-6-hydroxyethyl decahydroquinoline; 1-phenoxyethyl-2,2,4-trimethyl-6-ethoxy decahydroquinoline; 1-(6'-hydroxyhexyl)-2,4-dimethyl-2-ethyl-6-butoxy decahydroquinoline; 1-methyl-2,2,4-trimethyl-5-ethylcarbonyloxyethyl decahydroquinoline; 1-sec-butyl-2-methyl-2,4-dihexyl-6-hexylcarbonyloxydecyl decahydroquinoline; 1,2,2,4-tetramethyl-6-(3'-aminopropyl)-decahydroquinoline; 1-(2'-hydroxyethyl)-2,4-diethyl-2-methyl decahydroquinoline; 1-(2-hydroxy-3-phenoxypropyl)-2,2,4-trimethyl decahydroquinoline; 1-ethoxypropyl-2,2,4-trimethyl-7-heptyl decahydroquinoline; 1-(4'-chlorobutyl)-2,2,4trimethyl-6-cyclohexyl decahydroquinoline; 1-tetradecyl-2,2,4-trimethyl-6,8-diamino decahydroquinoline; 1-(4'-hydroxybutyloxahexyl)-2,4-dimethyl-2-ethyl-6-hydroxy decahydroquinoline; 1-[2'-hydroxyethyl-di-(oxaethyl)]-2,2,4-decahydroquinoline; 1-benzyl-2,2,4-trimethyl decahydroquinoline; 1-cyclohexylmethyl-2,2,4-trimethyl decahydroquinoline; 1,2,2,3,4-pentamethyl decahydroquinoline; 1-(3'-aminopropyl)-2,2,4-trimethyl decahydroquinoline; 1-(8'-cyanooctyl)-2,2,3-trimethyl-4-ethyl decahydroquinoline; 1-(2'-methylaminoethyl)-2,2-dihexyl-3-methyl-4-ethyl decahydroquinoline; 1-(2'-cyanoethyloxaethyl)-2,2,4-trimethyl decahydroquinoline; 1-n-propyl-2,2,3,4-tetramethyl-6-butoxy decahydroquinoline; 1-(2'-chloroethyl)-2,2,3,4-tetramethyl-6,8-diamino decahydroquinoline, and the like.

The more preferred substituted decahydroquinoline compounds are those wherein R is an alkyl of 1 to about 18 carbon groups, benzyl, cyclohexylmethyl, a hydroxyalkyl group of 1 to about 6 carbon atoms, a hydroxyalkyl ether group of 4 to about 12 carbon atoms, a cyanoalkyl group of 2 to about 6 carbon atoms, and an aminoalkyl group of 1 to about 6 carbon atoms; $R_a$, $R_b$ and $R_c$ are alkyl groups having 1 to about 12 carbon atoms; A is alkyl, alkoxy, cyclohexylalkyl, aminoalkyl, or alkylamino; $x$ is 0, 1, or 2; and wherein B is hydrogen or an alkyl group having 1 to about 12 carbon atoms.

Examples of these compounds are 1,2,2,4-tetramethyl decahydroquinoline; 1-ethyl-2,2,4-trimethyl decahydroquinoline; 1-decyl-2,2,4-trimethyl decahydroquinoline; 1-octyl-2-methyl-2,4-diethyl decahydroquinoline; 1-(2'-ethylhexyl)-2,2,4-trimethyl decahydroquinoline; 1-benzyl-2-methyl-2,4-dihexyl decahydroquinoline; 1-hexyl-2,2,4-triethyl decahydroquinoline; 1-(4'-cyanobutyl)-2-ethyl-2,4-dihexyl decahydroquinoline; 1,2,2-trimethyl-4-ethyl decahydroquinoline; 1-(4'-cyanobutyl)-2,2-diethyl-4-hexyl decahydroquinoline; 1-(2'-cyanoethyl)-2,2,4-trimethyl decahydroquinoline; 1,2,2,4-tetrahexyl decahydroquinoline; 1-(2'-aminoethyl)-2-methyl-2,4-diethyl decahydroquinoline; 1-(3'-aminopropyl)-2,2,4-trimethyl decahydroquinoline; 1-(2'-hydroxyethyl)-2,2,4-trimethyl decahydroquinoline; 1-[2'-hydroxyethyl-di-(oxaethyl)]-2,2,4-trimethyl decahydroquinoline; 1-(2'-hydroxypropyl)-2,2,4-trimethyl decahydroquinoline; 1-(2'-hydroxybutyl)-2,2,4-trimethyl decahydroquinoline; 1-(2'-hydroxyethyl)-2-methyl-2,4-diethyl decahydroquinoline; 1-(2'-hydroxyethyl)-2-methyl-2,4-dihexyl decahydroquinoline; 1-(2'-hydroxyethyl)-2,2,4,6-tetramethyl decahydroquinoline; 1,2,2,4,7-pentamethyl decahydroquinoline; 1-(2'-hydroxyethyl)-2,2,4-trimethyl-6-ethyl decahydroquinoline; 1-decyl-2,2-diethyl-4-methyl-6-nonyl decahydroquinoline; 1,2,2,4-tetramethyl-6-ethoxy decahydroquinoline; 1,2-diethyl-2,4-dimethyl-6-butoxy decahydroquinoline; 1-(4'-aminobutyl)-2,2,4-trimethyl-6-aminoethyl decahydroquinoline; 1,2-diethyl-2,4-dimethyl-5-butyl decahydroquinoline; 1-(2'-cyanoethyl)-2,2,4-trimethyl-6-methyl decahydroquinoline; 1-octyl-2,2,4-trimethyl-6-cyclohexylethyl decahydroquinoline; 1-(2'-aminoethyl)-2,2,3,4-tetramethyl decahydroquinoline; 1-(6'-hydroxyhexyl)-2-ethyl-2,3,4-trimethyl decahydroquinoline; 1-butyl-2-isobutyl-2,4-dimethyl-3-isopropyl decahydroquinoline; 1-(4'-hydroxybutyl)-2-methyl-2,4-dihexyl-3-ethyl decahydroquinoline; 1-(2'-cyanoethyl)-2-ethyl-2,3,4-trimethyl-6-ethoxy decahydroquinoline; 1-hexyl-2,2,3,4-tetramethyl-6-(3'-aminopropyl)decahyroquinoline; and the like.

Most preferred are those substituted decahydroquinoline compounds wherein R is an alkyl group, a hydroxyalkyl group, cyanoalkyl group, or an aminoalkyl group; $R_a$, $R_b$, and $R_c$ are alkyl groups of 1 to about 6 carbon atoms; A is an alkyl group of 1 to about 10 carbon atoms; $x$ is 0, 1, or 2; and B is hydrogen or a methyl or ethyl group. Examples of such compounds are given in the above listing. Excellent results have been obtained when using 1,2,2,4-tetramethyl decahydroquinoline, 1-ethyl-2,2,4-trimethyl decahydroquinoline, 1-decyl-2,2,4-trimethyl decahydroquinoline, 1-(2'-hydroxyethyl)-2,2,4-trimethyl decahydroquinoline, 1-(2'-hydroxyethyl)-2-methyl-2,4-diethyl decahyroquinoline, 1-(2'-hydroxyethyl)-2-methyl-2,4-dihexyl decahydroquinoline, 1-(2'-hydroxyethyl)-2,2,4,7-tetramethyl decahydroquinoline, 1-(2'-cyanoethyl)-2,2,4-trimethyl decahydroquinoline, and 1-(3'-aminopropyl)-2,2,4-trimethyl decahydroquinoline.

The substituted decahydroquinolines can be prepared by various methods. One particularly good method comprises a three-step process involving, first, the condensation reaction of an aromatic amine such as aniline or a ring-substituted aniline with a ketone or mixture of ketones to prepare a dihydroquinoline; second, hydrogenating the dihydroquinoline in the presence of a metal catalyst to yield the decahydroquinoline; and third, reaction at the nitrogen atom in the ring to form the 1-substituted product. A process to prepare the dihydroquinoline is disclosed in U.S. Pat. Nos. 3,829,292 and 3,910,918, and in J. Amer. Chem. Soc., Vol. 60 (1938) at pages 1458 et seq. Dihydroquinoline dimer products can also be prepared in the same reaction. A process of hydrogenating the dihydroquinoline to yield the decahydroquinoline is disclosed in U.S. Pat. Nos. 2,831,861 and 2,998,468.

As previously mentioned, dimer compounds and bis compounds of the novel substituted decahydroquinolines can also be prepared and used as effective UV stabilizers. Dimer and bis intermediate products can be prepared by hydrogenation of the unsaturated quinoline dimer or bis compound. For example, 6-[4'-(2,2,4-trimethyl-1,2-dihydroquinolyl)]-2,2,4-trimethyl-1,2-dihydroquinoline, which is the dimer of 2,2,4-trimethyl-1,2-dihydroquinoline (TMDQ) and which is prepared in small quantities as a by-product in the preparation of TMDQ, can be hydrogenated using a metal catalyst to yield a dimer compound, i.e., 6-[4'-(2,2,4-trimethyl-decahydroquinolyl)]-2,2,4-trimethyl decahydroquinoline. This compound can then be further reacted at the nitrogen atom to yield compounds of the invention. As a further example, in the article by D. Craig in the J. Amer. Chem. Soc., Vol. 60 (1938), page 1458 et seq., the author prepared the material 6,6'-methylene-bis-(2,2,4-trimethyl-1,2-dihydroquinoline). This material can be hydrogenated using a metal catalyst to yield a bis compound, i.e., 6,6'-methylene-bis-(2,2,4-trimethyl decahydroquinoline), which can then be further reacted at the nitrogen atom to yield a bis compound of the invention such as 6,6'-methylene-bis-(1-ethyl-2,2,4-trimethyl decahydroquinoline). In yet a further example, two moles of 2,2,4-trimethyl decahydroquinoline can be reacted with a dihaloalkane such as 1,10-dibromodecane to yield a bis compound of the invention, i.e., 1,10-bis-[1-(2,2,4-trimethyl decahydroquinolyl)]-decane. Other examples of dimer and bis compounds of the invention are 6-[4'-(1-ethyl-2,2,4-trimethyl decahyroquinolyl)]-1-ethyl-2,2,4-trimethyl decahydroquinoline; 8-[4'-(1-hydroxyethyl-2,2,4-trimethyl decahyroquinolyl)]-1-hydroxyethyl-2,2,4-trimethyl decahyroquinoline; 1,2-bis-[1-(2,2,4-trimethyl decahydroquinolyl)]ethane; 1,4-bis[1-(2-methyl-2,4-dihexyl decahydroquinolyl)]butane; 1,6-bis-[1-(2-methyl-2,4-diethyl decahydroquinolyl)]hexane; 1,6-bis-[4-(1,2,2,4-tetramethyl decahydroquinolyl)]hexane; bis-[2-(2,2,4-trimethyl decahydroquinolin-1-yl)ethyl]ether; bis-[4-(2-methyl-2,4-diethyl decahydroquinolin-1-yl)butyl]ether; bis-[2-(1,2-dimethyl-2-ethyl decahydroquinolin-4-yl)ethyl]sulfide; bis-[2-(1-hydroxy-ethyl-2,2-dimethyl decahydroquinolin-4-yl)ethyl]amine; 1,4-bis-[(2,2,4-trimethyl decahydroquinolin-1-yl)methyl]cyclohexane; 1,4-bis[2-(1,2,4-trimethyl-2-ethyl decahydroquinolin-6-yl)ethyl]benzene; and the like.

Detailed procedures to prepare the novel substituted decahydroquinolines of the invention are given in the examples.

The decahydroquinoline compounds of the invention are very efficient and effectual UV stabilizers for materials that are subject to light degradation. The substituted decahydroquinolines are used in the materials at a level of from about 0.05 part to about 10 parts by weight of compound per 100 parts by weight of the material. The use of over 10 parts by weight of the compound is not necessary to obtain the advantages of the invention. More preferably, the decahydroquinoline compounds are employed at a level of from about 0.1 part to about 5 parts by weight per 100 parts by weight of the material.

Materials that can be stabilized using the substituted decahydroquinolines include any material that demonstrates degradation on exposure to light, such as by discoloration and/or embrittlement. These materials can be low or high molecular weight materials, and particularly includes polymeric materials. Examples of materials that can be stabilized against degradation due to UV light are oils; monomers, particularly $\alpha,\beta$-olefinically unsaturated monomer such as acrylates, dienes, vinyl nitriles, and the like; and other lower molecular weight materials such as alcohols, aldehydes, and the like. Examples of polymeric materials that can be stabilized are natural rubber, synthetic rubbers such as cis-polyisoprene, styrene-butadiene rubber, diene-nitrile rubbers, polyepihalohydrin polymers, and the like, polyurethanes, PVC resins, ABS resins, polystyrene, polyacrylonitrile, polymethacrylates, polycarbonates, varnish, phenol-formaldehyde resins, polyepoxides, polyesters, and polyolefin homo- and copolymers such as polyethylene, polypropylene, ethylene-propylene polymers, ethylene-propylene-diene polymers, ethylene-vinyl acetate polymers, and the like. The decahydroquinoline compounds can also be used to stabilize mixtures and blends of polymeric materials such as ABS resin blends, PVC and polymethacrylate blends, and blends of polyolefin homopolymers and copolymers such as blends of polypropylene in epdm polymers.

The decahydroquinoline compounds of the invention are particularly useful as UV stabilizers for polyolefin homopolymers such as the poly-$\alpha$-monoolefin homopolymers. The $\alpha$-monoolefin monomers used to prepare the latter polymers include ethylene, propylene, isobutylene, 1-butene, 1-pentene, 1-hexene, 4-methyl-1-pentene, and the like. Excellent results have been obtained using the substituted decahydroquinoline compounds to stabilize polypropylene against UV degradation.

Many known compounding ingredients may be used along with the decahydroquinoline compounds in the compositions. Such ingredients include metal oxides such as zinc, calcium and magnesium oxide, fatty acids such as stearic and lauric acid, and salts thereof such as cadmium, zinc and sodium stearate and lead oleate; fillers such as calcium and magnesium carbonate, calcium and barium sulfates, aluminum silicates, asbestos, and the like; plasticizers and extenders such as dialkyl and diaryl organic acids like diisobutyl, diisooctyl, diisodecyl, and dibenzyl oleates, stearates, sebacates, azelates, phthalates, and the like; ASTM type 2 petroleum oils, paraffinic oils, castor oil, tall oil, glycerin, and the like; antioxidants such as 2,6-di-t-butyl paracresol, 2,2'-methylenebis-(4-ethyl-6-t-butyl phenol), 2,2'-thiobis-(4-methyl-6-t-butyl phenol), 2,2'-methylenebis-6-t-butyl-4-ethyl phenol 4,4'-butylidenebis-(6-t-butyl-m-cresol), 2-(4-hydroxy-3,5-di-t-butylanilino)-4,6-bis(octylthio)-1,3,5-triazine, hexahydro-1,3,5-tris-$\beta$-(3,5-di-t-butyl-4-hydroxyphenyl)propionyl-s-triazine, tris-(3,5-di-t-butyl-4-hydroxybenzyl)isocyanurate, tetrakismethylene-3(3',5'-di-t-butyl-4'-hydroxyphenyl)propionate methane, distearyl thiodipropionate, dilauryl thiodipropionate, tri(nonylphenylphosphite, tin thioglycolate, and the like; and other ingredients such as pigments, tackifiers, flame retardants, fungicides, and the like.

Compounding ingredients of particular interest to be used in the compositions of the invention are the antioxidant stabilizers. As the decahydroquinoline compounds of the invention are UV stabilizers, it is beneficial to add antioxidants to the compositions of the invention to achieve both UV light and oxygen stability of the compositions. The antioxidants are used in the range of from about 0.1 part to about 10 parts by weight, preferably from about 0.2 part to about 5 parts by weight per 100 parts by weight of the material. Of the types of antioxidants to be used, the phenolic antioxidants are preferred.

Examples of phenolic antioxidants are 2,6-di-t-butyl-phenol; 2-methyl-4,6-dinonyl phenol; 2,6-di-t-butyl-p-cresol; 2,2'-methylenebis(4-methyl-6-t-butyl phenol); 1,1'-methylenebis(2-naphthol); 4,4'-methylenebis(2,6-di-t-butyl phenol); 4,4'-thiobis(6-t-butyl-m-cresol); and the like. Although any phenolic antioxidant used in combination with the decahydroquinoline compounds would better the heat and oxygen stability of the compositions, the more preferred phenolic antioxidants are those having alkylhydroxyphenyl substituents on an ester or a heterocyclic nucleus.

Examples of phenolic antioxidants having alkylhydroxyphenyl substituents on an ester nucleus are compounds of the formula

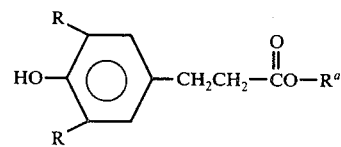

wherein R is hydrogen or an alkyl group of 1 to 9 carbon atoms, where at least one R must be an alkyl group, and $R^a$ is an alkyl group of 1 to 18 carbon atoms, exemplified by octadecyl 3-(3',5'-di-t-butyl-4'-hydroxyphenyl)propionate (see U.S. Pat. No. 3,330,859 for other examples); compounds of the formula

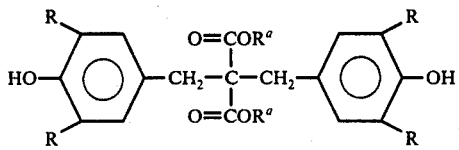

wherein R and R$^a$ are defined as above, exemplified by di-lauryl α,α'-bis(3,5-di-t-butyl-4-hydroxybenzyl)malonate (see U.S. Patent 3,627,725 for other examples); compounds of the formula

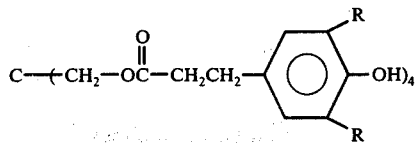

wherein R is defined as above, exemplified by tetrakis(-methylene-3-(3',5'-di-t-butyl-4'-hydroxyphenyl)propionate)methane; and the like.

Examples of phenolix antioxidant compounds having alkylhydroxyphenyl substituents on a heterocyclic nucleus are compounds where the heterocyclic nucleus is a triazine nucleus such as compounds of the formula

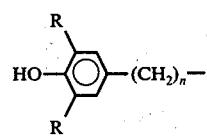

wherein X, Y, and Z are sulfur, oxygen, or nitrogen, and R is defined as above, exemplified by 2,4,6-tris(4-hydroxy-3,5-di-t-butyl benzylthio)-1,3,5-triazine (see British Patent No. 977,589 for other examples); compounds of the formula

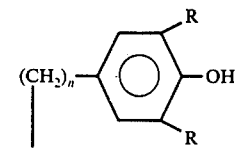

where R is defined as above, and $n$ is 0 to 6, exemplified by 2,4,6-tris(3',5'-di-t-butyl-4'-hydroxybenzyl)-1,3,5-triazine (see U.S. Pat. No. 3,706,740 for other examples); compounds of the formula

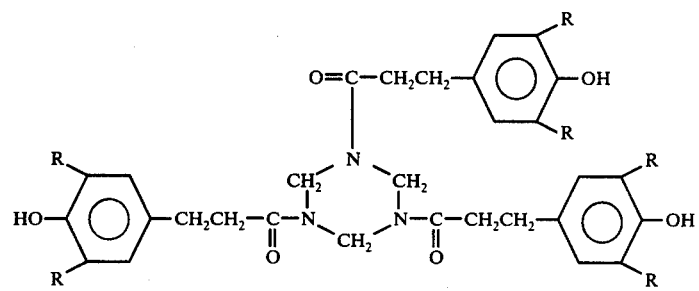

wherein R is defined as above, exemplified by hexahydro-1,3,5-tris-β-(3,5-di-t-butyl-4-hydroxyphenyl)propionyl-s-triazine (see U.S. Pat. 3,567,724 for other examples); compounds of the formula

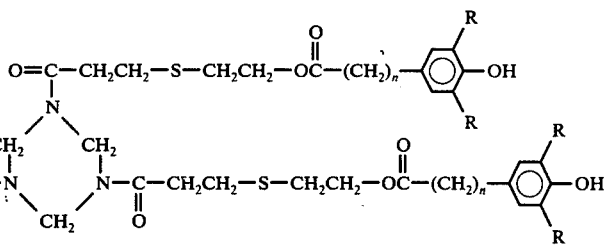

wherein R and $n$ are defined as above, exemplified by 1,3,5-tris(4'-hydroxy-3',5'-di-t-butylphenylpropionyloxyethylthiopropionyl)hexahydro-1,3,5-triazine (see U.S. Pat. No. 3,694,440 for further examples); and the like.

Examples of phenolic antioxidant compounds having alkylhydroxyphenyl substituents on an isocyanurate nucleus are compounds of the formula

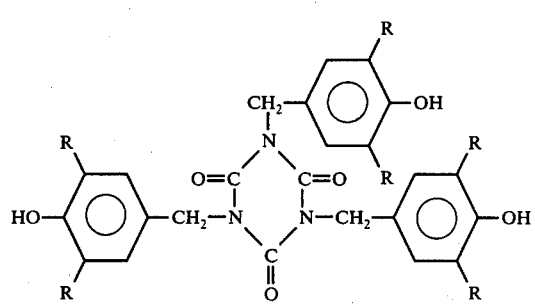

wherein R is defined as above, exemplified by tris-(3,5-di-t-butyl-4-hydroxybenzyl)isocyanurate (see U.S. Pat.

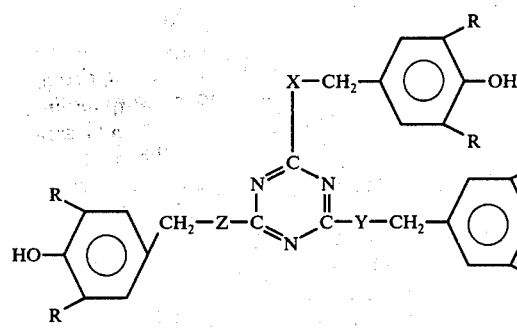

No. 3,531,483 for other examples); compounds of the formula

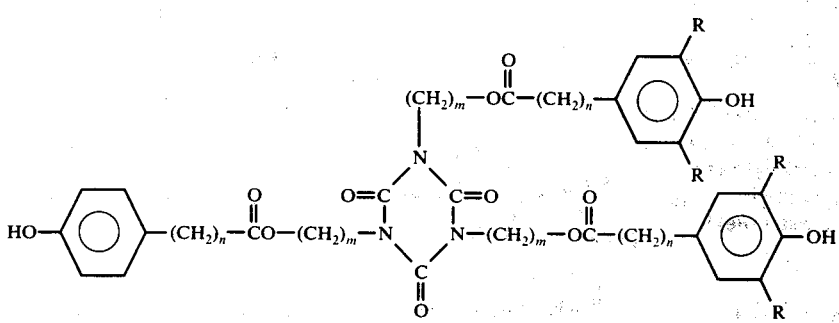

wherein R and n are defined as above, and m is 1 to 3, exemplified by 2,2′,2″-tris(3-(3,5-di-t-butyl-4-hydroxyphenyl)propionyloxy)ethyl isocyanurate (see U.S. Pat. No. 3,678,047 for further examples), and the like.

The combination of a decahydroquinoline compound and a phenolic antioxidant compound has particular utility for stabilizing polyolefinic polymers against degradation caused by heat, air (oxygen), and UV light.

The decahydroquinolines of the invention, and the other compounding ingredients if used, can be admixed with materials using known mixing techniques and equipment such as internal mixing kettles, a Banbury mixer, a Henschel mixer, a two-roll mill, an extruder mixer, or other standard equipment. Standard mixing times and temperatures can be employed. The objective is to obtain intimate and uniform mixing of the components. A favorable mixing procedure to use when adding the decahydroquinoline compound to a plastic material is to either dissolve or suspend the compound in a liquid such as hexane or benzene, add the plastic material in the form of a powder to the solution or suspension, evaporate off the liquid, and extruder mix the stabilized plastic material prior to forming the product.

The UV stability of a particular composition containing a polymeric material and a substituted decahydroquinoline can be evaluated by exposing a prepared sample of the composition to Xenon or Carbon Arc light in a Weather-Ometer operating at a temperature, for example, of about 140° F. (60° C.). Degradation of the sample can be followed by periodically measuring the carbonyl absorption band at 1720 cm$^{-1}$ using an IR Spectrophotometer. The rapid formation of carbonyl indicates failure of the sample. This test procedure is well known, and is published in the text Photodegradation, Photo-oxidation and Photostabilization of Polymers by Ranby and Rabek, John Wiley and Sons, N.Y., N.Y., (1975) at page 129 et seq., and is disclosed in U.S. Pat. No. 3,909,493. Failure of the sample is also checked by visual signs of cracking when the sample is bent 180°.

Samples of the compositions can also be checked for oxidative and thermal stability by measuring the time to discoloration and/or embrittlement of the sample after aging in an air circulating oven at 140° C.

EXAMPLES

The following examples are given to further illustrate the invention. Exact procedures for the preparation of the substituted decahydroquinoline compounds of the invention, preparation of sample compositions of the compounds and polymeric materials, and exact test procedures and test results are disclosed.

preparation of the Substituted Decahydroquinolines

The substituted decahydroquinolines of the invention are prepared by a number of different procedures including reaction between the liable hydrogen atom on the nitrogen with a compound such as an epoxide or a halide, and postreaction of decahydroquinoline compounds. Various methods will be given in the following examples. The saturated decahydroquinoline is prepared by catalytically hydrogenating the appropriate unsaturated quinoline. The appropriate unsaturated quinoline in turn is prepared by a condensation reaction between aniline or a substituted aniline and two ketones which may or may not be the same.

A method of preparing the starting material, i.e., the unsaturated quinoline, is disclosed in detail in U.S. Pat. Nos. 3,829,292 and 3,910,918, which method is hereby incorporated by reference. Generally, the reaction is an acid-catalyzed condensation reaction between an aniline and two ketones which can be depicted as follows:

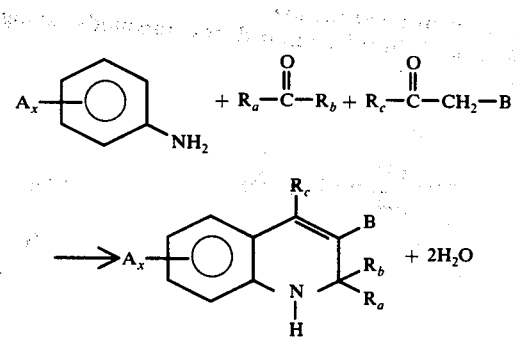

wherein $R_a$, $R_b$, $R_c$, A, B, and x are defined as first given above. This intermediate unsaturated quinoline is then heated in the presence of a metal catalyst and hydrogen to yield the completely saturated decahydroquinoline. As processes for preparing the unsaturated and saturated quinoline are known to the art, the following preparations will concentrate on the production of the nitrogen-substituted decahydroquinolines of the invention.

The metal catalysts useful to hydrogenate the unsaturated quinolines include reduced nickel, Raney nickel, rhodium, preferably deposited on a support such as charcoal, ruthenium, preferably deposited on a support such as charcoal, platinum oxide and palladium, preferably deposited on a support such as charcoal. The temperature of reaction is from about 20° C. to about 350° C. Times of reaction are from about 0.5 to 8 hours or more. High pressures, ranging up to 2000 psig are characteristic of the process.

EXAMPLE I

Preparation of the Intermediate Saturated Decahydroquinoline Compounds 2,2,4-trimethyl-1,2-dihydroquinoline (TMDQ) was obtained by the reaction between aniline and acetone. The chemical was a light yellow liquid having a boiling point of about 72° C. at 0.05 mm Hg.

The TMDQ prepared as above, 303 grams, was placed into a stainless steel autoclave along with 15 grams of Raney nickel. Hydrogen was then introduced into the closed autoclave to raise the internal pressure to 750 psig. The reaction mix was then heated to 220° C. while agitating the contents by shaking of the autoclave. Hydrogen was periodically introduced into the autoclave until the theoretical amount of hydrogen was taken up, about 3 hours. The reaction mix was then cooled and filtered to remove the catalyst. The chemical filtrate was analyzed by Carbon, Hydrogen, Nitrogen analysis and mass spectrometry and NMR spectroscopy, and shown to be the desired 2,2,4-trimethyldecahydroquinoline (a Perkin-Elmer Model 270 or duPont Model 21-490 mass spectrometer and a Varian A-60 NMR spectrometer were used). The product was 98.9% pure as determined by gas chromatography (a F and M Scientific Corp. Model 810 gas chromatograph using a 6 feet × 0.25 inch column packed with 10% OV-17 was used). The cis structure of the product was 91% as determined using an infrared spectrometer and measuring the IR bands at 607 $cm^{-1}$ for the cis and 637 $cm^{-1}$ for the trans and comparing the measurements to standards. The assignment of the cis and trans isomers is a tentative assignment based upon data obtained in studying decaline and decahydroquinoline and related compounds. Relative cis and trans contents of the decahydroquinolines were determined using the baseline technique of infrared spectroscopy. The cis structure shows a medium band at 607 $cm^{-1}$ while the trans structure shows a larger band at 637 $cm^{-1}$, both bands due to the >N-H motion being nonplanar. Furthermore, articles by B. Withop in the J. Amer. Chem. Soc, Vol. 70 (1948) at page 617 et seq. and by S. Mitsui et al in the J. of Catalysis, Vol. 30 (1975) at page 333 et seq. disclose that catalytic hydrogenation of closely related unsaturated products using certain specific metal catalysts such as platinum oxide or palladium yielded predominantly cis or trans isomers.

The above experiment was repeated using various catalysts and operating at different temperatures, pressures, and times. Results obtained were as follows:

1. Using 9.0 grams of a catalyst of 5% by weight of ruthenium on carbon and a reaction temperature of 220° C., 2,2,4-trimethyldecahydroquinoline of 98% purity and 94% cis structure was prepared in about 2.5 hours.

2. Using a catalyst of 3 grams of rhodium at 5% by weight on carbon and a reaction temperature of 200° C., 2,2,4-trimethyldecahydroquinoline of 98% purity and 96% cis structure was prepared in about 1.75 hours.

3. Using 5 grams of platinum oxide as the catalyst, operating at a temperature of 150° C. and employing 120 milliliters of glacial acetic acid as a reaction medium, 139 grams of TMDQ was reacted in about 5.5 hours to form 18.7 grams of 2,2,4-trimethyldecahydroquinoline having a 96% cis structure.

4. Using 12 grams of a Raney nickel catalyst and operating at a temperature of 200° C., in 3 hours, 2,2,4-trimethyldecahydroquinoline of 99% purity and 77% cis structure was obtained.

5. Using 10.4 grams total of reduced nickel as the catalyst (Harshaw Ni-0104p) and operating at 200° C. over about 26 hours, 2,2,4-trimethyldecahydroquinoline having a 40% cis content was obtained.

The above experiments were repeated using various catalysts, various operating conditions, and using different unsaturated quinolines. Thus, the following intermediate saturated decahydroquinolines were prepared:

6. 2-methyl-2,4-diethyl-1,2-dihydroquinoline, 250 grams, was placed in a reactor along with 3 grams of rhodium at 5% by weight on charcoal. Hydrogen was introduced to the reactor such that an internal pressure of 1000 psig existed at a reaction temperature of 190° C. Reaction time was 6 hours. The recovered product has an NMR spectra consistent with the desired product, 2-methyl-2,4-diethyldecahydroquinoline. The compound has a boiling point of 85° C. at 1 mm of Hg and was analyzed as 90% pure via vapor pressure chromotography. Carbon, hydrogen, nitrogen content for the formula $C_{14}H_{27}N$ is 80.31% carbon, 13.00% hydrogen, and 6.69% nitrogen and the analyzed values were 80.61% carbon, 13.47% hydrogen, and 6.35% nitrogen.

7. Following the procedure given in the preceding example, 65 grams of 2-methyl-2,4-dihexyl-1,2-dihydroquinoline was reacted with hydrogen in the presence of 2 grams of rhodium at 5% by weight on charcoal, at a temperature of 200° C. and a pressure of 1000 psig for 2.5 hours, to yield 2-methyl-2,4-dihexyldecahydroquinoline of 94% purity (as determined by vapor pressure chromotography). The product has a boiling point of 170° C. at 1 mm of Hg and has an NMR spectra consistent with the desired structure.

8. 2,2,4,7-tetramethyldecahydroquinoline was prepared by reacting 125 grams of 2,2,4,7-tetramethyl-1,2-dihydroquinoline with hydrogen using 3 grams of rhodium at 5% by weight on charcoal as the catalyst and operating at 185° C., a 1000 psig pressure, for 24 hours. The desired product was confirmed by NMR spectral analysis and its carbon, hydrogen, nitrogen content (calculated contents for $C_{13}H_{25}N$ is the same as above and analyzed contents were 78.95% carbon, 13.30% hydrogen, and 6.80% nitrogen). The product was 95% pure as determined by vapor pressure chromotograhy and boiled at about 65° C. at 1 mm of Hg.

9. 2,2,4,8-tetramethyldecahydroquinoline was prepared by reacting 74 grams of 2,2,4,8-tetramethyl-1,2-dihydroquinoline with hydrogen in the presence of 2 grams of rhodium at 5% by weight on charcoal at a temperature of 200° C., a pressure of 1000 psig, and over a period of 8 hours. The desired product was confirmed by NMR spectral analysis and carbon, hydrogen, nitrogen analysis (calculated content for $C_{13}H_{25}N$ is the same as above and analyzed contents were 80.03% carbon, 13.38% hydrogen, and 6.09% nitrogen). The product was 90% pure as determined by vapor pressure chromotography and boiled at 65° C. at 0.6 mm of Hg.

10. The dimer of 2,2,4-trimethyldecahydroquinoline was prepared by hydrogenation of the dimer of the unsaturated quinoline. In the process of preparing 2,2,4-trimethyl-1,2-dihydroquinoline (TMDQ) an amount of the dimer product is also formed. This TMDQ dimer can be separated out of the TMDQ and itself used to prepare substituted decahydroquinolines of the invention. 6-[4'-(2,2,4-trimethyl-1,2-dihydroquinolyl)]-2,2,4-trimethyl-1,2-dihydroquinoline was obtained by distillation and separation of the chemical from the reaction mix of a 2,2,4-trimethyl-1,2-dihydroquinoline preparation. The chemical had a boiling point of 198° C. at 1.3 mm Hg. The chemical was placed in an autoclave with hydrogen and a catalyst of rhodium at 5% by weight on charcoal. Reaction temperature was 210° C. and internal pressure was 2000 psig. After 24 hours, the reaction mix was cooled down, the catalyst filtered out, and the liquid subjected to distillation. A liquid fraction boiling at 190° C. at 1 mm Hg was collected and analyzed. The IR spectra and NMR spectra of the liquid was consistent with the desired product, 6-[4'-(2,2,4-trimethyl-decahydroquinolyl)]-2,2,4-trimethyldecahydroquinoline. The calculated carbon, hydrogen, nitrogen content of the $C_{24}H_{44}N_2$ compound is 79.93% carbon, 12.30% hydrogen, and 7.77% nitrogen while the analyzed contents were 80.30% carbon, 12.43% hydrogen, and 7.63% nitrogen.

Similarly, other unsaturated hydroquinoline dimer and bis products can be hydrogenated to prepare the dimer and bis compounds. 6,6'-methylene-bis-(2,2,4-trimethyl-1,2-dihydroquinoline), prepared following the procedure given in the article in J. Amer. Chem. Soc., Vol. 60 (1938) at page 1458 et seq., can be reacted with hydrogen in the presence of rhodium as the catalyst to yield 6,6'-methylene-bis-(2,2,4-trimethyldecahydroquinoline).

Similarly, yet other forms of the intermediate saturated decahydroquinolines were prepared. Some of these materials were then used in the following examples to prepare the novel substituted decahydroquinolines of the invention.

EXAMPLE II 1,2,2,4-tetramethyl decahydroquinoline was prepared. 36.3 grams (0.2 mole) of 2,2,4-trimethyl decahydroquinoline of about 58% cis structure was placed in a reactor vessel equipped for agitation. Formic acid, 20.2 grams (0.44 mole) was added dropwise to the reactor vessel followed by the slow addition of 17.4 grams of 38% by weight formaldehyde in water solution. After addition, the mix was refluxed at for 4 hours. A 5N sodium hydroxide solution was then added until the mix was basic. Diethyl ether was added and the mix separated out and the ether fraction obtained. The fraction was concentrated and then distilled using a 3 inch Vigreaux column to yield 5.4 grams of a product boiling at 70° C. at 0.6 mm Hg. The NMR spectra of the product was consistent with the desired product, 1,2,2,4-tetramethyl decahydroquinoline. The theoretical carbon, hydrogen, nitrogen analysis for the formula $C_{13}H_{25}N$ is 79.92% carbon, 12.90% hydrogen, and 7.17% nitrogen while measured values were 77.23% carbon, 13.13% hydrogen, and 6.56% nitrogen.

EXAMPLE III 1-ethyl-2,2,4-trimethyl decahydroquinoline was prepared by the reaction of the intermediate saturated decahydroquinoline with the alkyl halide. 36.3 grams (0.2 mole) of 2,2,4-trimethyl decahydroquinoline of about 76% cis structure was placed into a reactor vessel equipped for heating and agitation. 15.6 grams (0.1 mole) of iodoethane was added dropwise to the reactor vessel. The mix was heated to 105° C. while stirring for 3 hours. A thick slurry formed which was filtered out and washed wih acetone. The acetone wash liquid was then concentrated and distilled using a 3 inch Vigreaux column to yield 7.1 grams of a product boiling at 58° – 60° C. at 0.25 mm Hg. The NMR spectra of the product was consistent with the desired product, 1-ethyl-2,2,4-trimethyl decahydroquinoline. Calculated carbon, hydrogen, nitrogen content for the formula $C_{14}H_{27}N$ is 80.31% carbon, 13.00% hydrogen, and 6.69% nitrogen while the measured contents were 79.93% carbon, 13.54% hydrogen, and 6.35% nitrogen respectively.

EXAMPLE IV

Following the procedure given in Example III, 36.3 grams (0.2 mole) of 2,2,4-trimethyl decahydroquinoline was reacted with 22.12 grams (0.1 mole) of 1-bromodecane at 155° C. for 7 hours. A thick slurry formed which was filtered out, 2 milliliters of 1-bromodecane was added to the filtrate and the mixture heated at 150° C. for about 40 hours. The mixture was then washed with benzene and the benzene wash liquid itself washed twice with water and then concentrated. The concentrate was distilled to yield 13.2 grams of a product boiling at 130° C. at 0.11 mm Hg. The NMR spectra was consistent with that of the desired product, 1-n-decyl-2,2,4-trimethyl decahydroquinoline. The carbon, hydrogen, nitrogen content for the formula $C_{22}H_{43}N$ is 82.17% carbon, 13.48% hydrogen, and 4.36 nitrogen while the measured contents were 82.76% carbon. 13.91% hydrogen, and 4.28% nitrogen.

EXAMPLE V

A series of 1-hydroxyalkyl substituted decahydroquinolines was prepared. The preparation basically involved a reaction between the liable hydrogen atom on the nitrogen and an epoxy group. The following compounds were prepared.

A. 1-(2'-hydroxyethyl)-2,2,4-trimethyl decahydroquinoline was prepared. 150 milliliters of ethanol and 84.0 grams (0.3 mole) of 2,2,4-trimethyl decahydroquinoline of about 96% cis structure were placed in a reactor vessel equipped for heating and agitation. 15.4 grams (0.35 mole) of ethylene oxide was added dropwise to the reactor vessel and the mix then heated to reflux for 21 hours. The ethanol was then evaporated off and the reaction mixture distilled to yield 10.2 grams of a liquid product boiling at 103° – 105° C. at 0.3 mm Hg. The NMR and mass spectrometer spectra were consistent with the desired product. Calculated contents for the formula $C_{14}H_{27}NO$ are 74.61% carbon, 12.08% hydrogen, and 6.22% nitrogen and the measured contents were 74.62% carbon, 12.11% hydrogen, and 6.13% nitrogen.

The above experiment was repeated at more optimum reaction conditions. 276.1 grams (1.5 moles) of 2,2,4-trimethyl decahydroquinoline of about 94% cis structure was placed into the reactor vessel along with 73.8 grams (1.67 moles) of ethylene oxide, 10.0 grams of ethanol, and 1.0 gram of p-toluene sulfonic acid. The mix was heated to 180° C. for 5 hours. The reaction mixture was then distilled using a 14 inch column packed wih stainless steel packing to yield 269.2 grams of a liquid fraction boiling at about 92° to 111° C. at 0.08 to 0.10 mm Hg. The fraction was about 97% pure as determined by gas chromatography. The fraction was again distilled to yield 201.5 grams of product boiling at 97° C. at 0.09 mm Hg. which was over 99% pure 1-(2'-hydroxyethyl)-2,2,4-trimethyl decahydroquinoline as determined by gas chromatography.

The preparations given above were essentially repeated using 2,2,4-trimethyl decahydroquinoline of about 75% cis and about 40% cis structure. Yields of 1-(2'-hydroxyethyl)-2,2,4-trimethyl decahydroquinoline in each case were about 90 ± 2% of theoretical yield based on the amount of saturated intermediate compound used.

B. 1-(2'-hydroxypropyl)-2,2,4-trimethyl decahydroquinoline was prepared by the reaction of 30.2 grams (0.52 mole) of propylene oxide with 90.7 grams (0.5 mole) of 2,2,4-trimethyl decahydroquinoline of about 75% cis structure in the presence of 3 grams of ethanol at 170° C. for 49 hours. The reaction mix was distilled using a 4 inch Vigreaux column to yield 73.1 grams of the desired product, boiling at 93° to 96° C. at 0.26 mm Hg. The NMR and mass spectrometer spectra were consistent with the desired product. The formula $C_{15}H_{29}NO$ has calculated contents of 75.25% carbon, 12.21% hydrogen, and 5.85% nitrogen and the measured contents were 75.42% carbon, 12.77% hydrogen, and 5.62% nitrogen.

C. Following the procedures given above, 2,2,4-trimethyl decahydroquinoline of about 76% cis structure was reacted with 1,2-epoxybutane in the presence of ethanol to yield 58 grams of 1-(2'-hydroxybutyl)-2,2,4-trimethyl decahydroquinoline, which had a boiling point of 110° – 112° C. at 0.50 mm Hg. Calculated contents for the formula $C_{16}H_{31}NO$ were 75.83% carbon, 12.33% hydrogen, and 5.53% nitrogen and the measured values were 76.55% carbon, 13.13% hydrogen, and 5.49% nitrogen.

D. 1-(2'-hydroxy-3'-phenoxy propyl)-2,2,4-trimethyl decahydroquinoline was prepared using a process similar to those described above. 27.2 grams (0.15 mole) of about 75% cis structure 2,2,4-trimethyl decahydroquinoline was reacted with 22.5 grams (0.15 mole) of 1,2-epoxy-3-phenoxy propane in the presence of 0.5 gram of ethanol at 160° C. for 19 hours. The reaction mixture was distilled to yield 21.2 grams of a liquid product boiling at 168° C. at 0.2 mm Hg. The infrared and mass spectrometer spectra are consistent with the desired product. Calculated values for $C_{21}H_{34}NO_2$ were 75.85% carbon, 10.31% hydrogen, and 4.21% nitrogen, while measured values were 74.67% carbon, 10.18% hydrogen, and 4.26% nitrogen.

E. 1-(2'-hydroxyethyl)-2,2,4,6-tetramethyl decahydroquinoline was prepared. 50 grams of 2,2,4,6-tetramethyl decahydroquinoline and 50 milliliters of 1-octanol were placed into a reactor vessel equipped for heating and agitation and he mix heated to 200° C. Ethylene oxide was then slowly added to the reactor over a period of 7 hours. The reaction mixture was then distilled to yield a liquid product boiling at 106° C. at 0.5 mm Hg. The NMR and infrared spectra were consistent with the desired product. Calculated contents and analyzed contents of the product (formula of $C_{15}H_{29}NO$) were respectively: 75.26% carbon, 74.36% carbon found; 12.21% hydrogen, 12.24% hydrogen found; and 5.85% nitrogen, 6.04% nitrogen found.

F. Following the procedure given in E above, 75 grams of 2-methyl-2,4-diethyl decahydroquinoline were reacted with ethylene oxide in the presence of 50 milliliters of ethylene glycol at 200° C. for 10 hours to yield 1-(2'-hydroxyethyl)-2-methyl-2,4-diethyl decahydroquinoline, which had a boiling point of 140° C. at 0.8 mm Hg. The NMR and infrared spectra were consistent with the desired product. For formula of $C_{16}H_{31}NO$, the calculated carbon, hydrogen, nitrogen contents are 75.83% carbon, 12.33% hydrogen, and 5.53% nitrogen and the analyzed contents were 74.69% carbon, 12.24% hydrogen, and 5.14% nitrogen.

G. Following the above procedures, 25 grams of 2-methyl-2,4-dihexyl decahydroquinoline in 50 milliliters of 1-octanol was reacted with ethylene oxide at 200° C. for 8 hours to yield 1-(2'-hydroxyethyl)-2-methyl-2,4-dihexyl decahydroquinoline which had a boiling point at 192° C. at 0.7 mm Hg. The products NMR and infrared spectra were consistent with the desired product.

H. 1-(2'-hydroxyethyl)-2,2,4,7-tetramethyl decahydroquinoline was prepared. 75 grams of 2,2,4,7-tetramethyl decahydroquinoline in 50 milliliters of ethylene glycol was reacted with ethylene oxide added over a period of 14 hours at a reaction temperature of 200° C. The reactor mix was distilled to yield a liquid product which boiled at 102° C. at 0.1 mm of Hg and which was 98% pure as determined by vapor pressure chromatography. The infrared and NMR spectra were consistent with the desired product. Calculated contents for the formula $C_{15}H_{29}NO$ are 75.26% carbon, 12.21% hydrogen, and 5.85% nitrogen while measured contents were 74.78% carbon, 12.30% hydrogen, and 5.50% nitrogen.

I. Following the procedure in H above, 1-(2'-hydroxyethyl)-2,2,4,8-tetramethyl decahydroquinoline was prepared by reacting 2,2,4,8-tetramethyl decahydroquinoline with ethylene oxide. The product has a melting point of 72° to 75° C., and was confirmed by its NMR and infrared spectra.

EXAMPLE VI 2,2,4-trimethyl decahydroquinoline, 22 grams, was placed in a reactor vessel equipped for heating and agitation along with 26 grams of α-bromotoluene, 200 milliliters of dioxane, and 10 grams of anhydrous potassium carbonate. The mixture was heated to reflux and stirred for 36 hours. The reaction mix was then distilled to yield a liquid product boiling at 190° C. at 10 mm Hg. The NMR and infrared spectra were consistent with the desired product, 1-benzyl-2,2,4-trimethyl decahydroquinoline. The formula $C_{19}H_{29}N$ has a content of 84.07% carbon, 10.77% hydrogen, and 5.16% nitrogen and the analyzed contents were 84.39% carbon, 10.25% hydrogen, and 4.46% nitrogen.

EXAMPLE VII

In addition to saturated aliphatic substituents at the 1-position on the nitrogen atom, such as alkyl and hydroxyalkyl or ether groups, unsaturated aliphatic groups can be substituted at the 1-position and bis products can be prepared. The following example demonstrates this.

36.3 grams (0.2 mole) of the intermediate compound, 2,2,4-trimethyl decahydroquinoline of about 58% cis structure, was placed into a reactor vessel equipped for heating and agitation. 15.0 grams (0.05 mole) of 1,10-dibromodecane was added dropwise to the reactor and the mixture heated to 140° ± 10° C. for 48 hours. The reaction mix was in the form of a slurry. The particulate material was filtered out and washed with acetone, and the acetone wash liquid saved. Both the acetone wash liquid and the filtrate from the reaction slurry were concentrated, together, and then distilled using a 3 inch Vigreaux column. 10.5 grams of a liquid product boiling at 155° – 157° C. at 0.40 mm Hg. was obtained. The liquid product was analyzed by NMR and shown to contain a mixture of about 72 mole percent 1-(9'-decenyl)-2,2,4-trimethyl decahydroquinoline and about 28 mole percent of 1,10-bis-[1-(2,2,4-trimethyl decahydroquinolyl)]-decane. The latter bis-product was also confirmed by mass spectrometer analysis.

EXAMPLE VIII

The novel decahydroquinolines of the invention having hydroxyalkyl groups at the 1-position are not only excellent UV stabilizers in their own right, but also can be post-reacted to provide yet new and different decahydroquinoline compounds that are also effective UV stabilizers, and also can be further post-reacted. The following examples show the preparation of such compounds.

1-(2'-chloroethyl)-2,2,4-trimethyl decahydroquinoline was prepared. 184.8 grams (0.82 mole) of 1-(2'-hydroxyethyl)-2,2,4-trimethyl decahydroquinoline prepared above was placed along with 400 milliliters of benzene in a reactor equipped for heating and cooling and for agitation. Thionyl chloride, 130 grams (1.0 mole) was then added dropwise to the reactor vessel over a period of 2 hours while maintaining the temperature of the reaction mix at 32 ± 2° C. The reaction mix was then heated to 68° C. for 3 hours. 1 mole of a 30% by weight aqueous solution of NaOH was then added to the reactor vessel and the mixture stirred for about 25 minutes. A slurry formed which was filtered out. The benzene phase in the filtrate was separated from the aqueous phase and the aqueous phase was washed four times with benzene. The original benzene phase and the benzene washes were combined, concentrated, and then distilled using a 9 inch Vigreaux column to yield 159.1 grams of a liquid product boiling at 88° to 89° C. at 0.3 mm Hg. The infrared and mass spectrometer spectra were consistent with the desired product, 1-(2'-chloroethyl)-2,2,4-trimethyl decahydroquinoline. The carbon, hydrogen, nitrogen, chlorine content of the formula $C_{14}H_{26}ClN$ is 68.96% carbon, 10.75% hydrogen, 14.54% chlorine, and 5.75% nitrogen, while the analyzed values of the product were 69.14% carbon, 10.77% hydrogen, 14.82% chlorine, and 5.74% nitrogen.

EXAMPLE IX 1-(2'-cyanoethyl)-2,2,4-trimethyl decahydroquinoline was prepared via the post-reaction of the above chloroethyl substituted compound. 61.0 grams (0.25 mole) of 1-(2'-chloroethyl)-2,2,4-trimethyl decahydroquinoline dissolved in 50 milliliters of methyl sulfoxide was added dropwise over a period of 40 minutes at room temperature to a prepared solution of 12.25 grams (0.25 mole) of sodium cyanide in 150 milliliters of methyl sulfoxide. The mix was then heated to 95° C. and stirred for 2.5 hours. The reaction mixture was then cooled, poured into 500 milliliters of ice water, diethyl ether was added, the organic layer separated out. The aqueous layer was washed with four 100 milliliter portions of diethyl ether and the ether washes combined wih the original organic layer. The solution was then concentrated and distilled using a 6 inch Vigreaux column to yield 43.0 grams of a liquid product boiling at 134° – 136° C. at 3.3 mm Hg. The infrared spectrum of the product is consistent with the desired compound, 1-(2'-cyanoethyl)-2,2,4-trimethyl decahydroquinoline. Calculated values for the formula $C_{15}H_{26}N_2$ are 76.87% carbon, 11.18% hydrogen, and 11.95% nitrogen and found contents were 76.71% carbon, 11.02% hydrogen, and 11.15% nitrogen.

EXAMPLE X

Using the cyanoethyl nitrogen-substituted compound prepared in Example IX as a starting material, an aminoalkyl nitrogen-substituted decahydroquinoline compound was prepared. 23.3 grams (0.1 mole) of 1-(2'-cyanoethyl)-2,2,4-trimethyl decahydroquinoline was placed in a reactor vessel equipped for heating and agitation. A solution of 3.8 grams (0.1 mole) of lithium aluminum hydride in 100 milliliters of diethyl ether was then added. The reaction mix was stirred, as it was a slurry, and a suspension of 13.3 grams (0.1 mole) of aluminum chloride in 150 milliliters of diethyl ether was added dropwise to the reactor. After 3 hours, ethyl acetate was added to destroy any unreacted lithium aluminum hydride. 100 milliliters of water and 140 milliliters of 6N sulfuric acid were added to the reaction mixture and it separated into an aqueous phase and an organic phase. The organic phase was separated out and washed with water. It was then cooled in an ice bath and KOH added until the pH reached 11. 400 milliliters of water was then added, followed by four 100 milliliter washes with diethyl ether. The ether extracts and washes were combined, filtered, concentrated to a syrup, and then distilled using a 6 inch Vigreaux column to yield a liquid product boiling at 162° to 184° C. to 0.5 mm Hg. The NMR spectra was consistent with the desired product, 1-(3'-aminopropyl)-2,2,4-trimethyl decahydroquinoline.

EXAMPLE XI

A mixture of 63 grams (0.4 mole) of 2,2,4-trimethyl decahydroquinoline, 78 grams (0.2 mole) of 3-epoxyethyl-7-oxabicyclo [4.1.0] heptane, and 2 milliliters of ethylene glycol were placed in a reactor vessel and heated to reflux for 12 hours. The reactor mix was then distilled under reduced pressure to yield a liquid product boiling at 160° – 180° C. at 0.5 to 1 mm of Hg. The structure of the product was consistent with that of the desired product, 1-[2'-hydroxy-2'-(3,4-epoxycyclohexyl)ethyl]-2,2,4-trimethyldecahydroquinoline, as determined by NMR and infrared spectroscopy. Calculated contents for the formula $C_{20}H_{35}NO_2$ are 74.72% carbon, 10.97% hydrogen, and 4.35% nitrogen while actual measured values were 75.47% carbon, 11.28% hydrogen, and 4.30% nitrogen.

Sample Preparation and Evaluation of Substituted Decahydroquinolines

The decahydroquinoline compounds prepared in the preceding examples were evaluated as UV stabilizers for polymeric materials subject to light degradation. The evaluation was conducted by measuring the UV stability of compositions of unstabilized polypropylene and the decahydroquinolines on exposure to light from either a Carbon Arc or Xenon light source. The sample compositions evaluated contained a small level of a known antioxidant to allow for preparation and processing of the sample compositions without significant thermal and oxidative degradation occurring. The antioxidant used alone in the polypropylene had little effect on the UV stability of the composition.

Preparation of the sample compositions was as follows: Unstabilized polypropylene (Profax 6501 sold by Hercules, Inc.) in powder form was employed in the tests. The antioxidant and substituted decahydroquinolines were admixed with the polypropylene (PP) homopolymer at levels of 0.25 gram to 0.5 gram of antioxidant and 0.25 gram to 1 gram of decahydroquinoline compound per 100 grams of PP using the following procedure. The antioxidant and substituted decahydroquinoline were dissolved in 300 milliliters of a solvent such as benzene and then 200 grams of PP in powder form was added. The benzene was then evaporated off under reduced pressure and the resulting admixture then extruded using a Brabender extruder operating at 450° F. (232° C.) and at about 75 rpm. Sample compositions were obtained from the middle portion of the extrudate.

Test samples were prepared from the sample compositions by molding the compositions between aluminum plates at 420° F. (215° C.) using a pressing cycle of 1 minute heat up, 3 minutes under 20,000 psig molding pressure, and 4 minutes cool down. The molded test sheets, which were 10 to 20 mils thick, were cut into 2 inch by 1 inch strips and mounted for subsequent exposure to light.

The test samples were evaluated using an Atlas Model 60-W Weather-Ometer operating at 140° to 150° F. (60° to 63° C.) using either a Carbon Arc or a Xenon light source. UV light degradation of the test sample compositions was measured by following the infrared absorption band of the sample at 1720 $cm^{-1}$, which band corresponds to carbonyl formation. A Perkin Elmer model 467 IR Spectrophotometer was employed. This test procedure is disclosed in U.S. Pat. No. 3,909,493 and is published in the text *Photodegradation, Photo-oxidation and Photostabilization of Polymers* by Ranby and Rabek, John Wiley and Sons, N.Y., N.Y. (1975) at page 129 et seq. In general, the test procedure involves the recordation of the initial absorbance ($A_o$) of the test sample at 1720 $cm^{-1}$ followed by periodic measurement of the 1720 $cm^{-1}$ band at subsequent exposure times ($A_t$). A plot of the change in the sample of absorbance ($A_t$-$A_o$) versus time will show a substantially linear portion wherein little or no change in absorbance occurs on exposure followed by a second substantially linear portion wherein rapid change of absorbance versus time occurs. The point of intersection of a straight line drawn to each portion of the plot indicates the time at which rapid carbonyl formation initiates in the polymeric material (herein PP). Rapid carbonyl formation is evidence of UV initiated degradation of the test sample, which can also be correlated to visible signs of degradation such as darkening and discoloration and embrittlement of the sample. Time to failure of the test sample is taken to be the total time from initial exposure to the time of rapid carbonyl formation as determined by the above test method.

In addition to evaluating UV stability, the oxidative and thermal stability of many of the test samples were also measured. The test comprised heat aging test samples of the compositions in an air-circulating oven at 284° F. (140° C.) and measuring the time to complete embrittlement of the sample as evidenced by crumbling of the test sample.

EXAMPLE XII

In this example, various hydroxyalkyl-substituted decahydroquinolines were evaluated as UV stabilizers in polypropylene. The sample compositions were prepared following the procedure which was previously disclosed. A small amount (0.25 part per 100 parts of PP) of antioxidant was included in some compositions to reduce oxidative/thermal degradation from occurring in the preparation of the samples. The test samples were exposed to UV light from a Xenon light in a Weather-Ometer operating at 140° F. (60° C.). Results are given in the following table. All of the decahydroquinoline compounds exhibited excellent ability to provide protection for a material against UV light.

| Sample | Compound (Level in parts/100) | Time to Failure (Hours) |
|---|---|---|
| Control[1] | — | 140 |
| A[1] | 1-(2'-hydroxyethyl)-2,2,4-trimethyl decahydroquinoline (0.25) | 780 |
| B | 1-(2'-hydroxyethyl)-2,2,4,6-tetramethyl decahydroquinoline (0.5) | 930 |
| C | 1-(2'-hydroxyethyl)-2-methyl-2,4-dihexyl decahydroquinoline (0.5) | 790 |
| D | 1-(2'-hydroxyethyl)-2-methyl-2,4-diethyl decahydroquinoline (0.5) | 800 |
| X | Tinuvin 327[2] (0.5) | 690 |

[1]no antioxidant present in composition
[2]2-(3',5'-di-t-butyl-4-hydroxyphenyl)-5-chlorobenzotriazole

EXAMPLE XIII

Other novel decahydroquinoline compounds of the invention were evaluated as UV stabilizers. The following sample compositions were prepared and evaluated following the procedures previously given. The test samples were exposed to UV light from a Xenon light in a Weather-Ometer operating at 140° F. (60° C.). Each sample contained 100 parts by weight of polypropylene and 0.25 part by weight of a thermal/oxidative stabilizer, Irganox 1010, tetrakis [methylene-(3,5-di-t-butyl-4-hydroxyhydrocinnamate)]methane. Results, which are given in the following table, show that the compounds of the invention are excellent UV stabilizers. Thermal/oxidative aging tests are also conducted and the results shown.

| Sample | Compound (Used at 0.5 part/100 parts PP) | Time to Failure (Hours) | Oven Aging (Hours) |
|---|---|---|---|
| Control | — | 190[a] | 2350 |
| A | 1-(2'-hydroxyethyl)-2,2,4-trimethyl decahydroquinoline | 1460[a] | 2280[a] |
| B | 1-(2'-hydroxybutyl)-2,2,4-trimethyl decahydroquinoline | 1740 | 2616 |
| C | 1-(2'-hydroxyethyl)-2,2,4,8-tetramethyl decahydroquinoline | over 6021 | 2760 |
| D | 1-(2'-hydroxy-3-phenoxypropyl)-2,2,4-trimethyl decahydroquinoline | 1300 | 2180 |
| E | 1-(2'-chloroethyl)-2,2,4-trimethyl decahydroquinoline | 350 | 2760 |

[a]Averaged data from two tests

EXAMPLE XIV

The substituted decahydroquinoline compounds of the invention are excellent UV stabilizers for polyolefin plastics. The results in the following table show that these compounds are comparable to or better than a well known UV stabilizer in their ability to protect polypropylene from UV degradation. The sample compositions were prepared and evaluated as described in Example XII. Each sample contained 100 parts by weight of polypropylene, 0.25 part by weight of Irganox 1010, and 0.50 part by weight of UV stabilizer.

| Sample | UV Stabilizer | Time to Failure (Hours) | Oven Aging (Hours) |
|---|---|---|---|
| Control | — | 190$^a$ | 2350 |
| A | 1-(2'-hydroxyethyl)-2,2,4-trimethyl decahydroquinoline | 1460$^a$ | 2280$^a$ |
| B | 1-(2'-hydroxybutyl)-2,2,4-trimethyl decahydroquinoline | 1740 | 2620 |
| C | Tinuvin 327$^b$ | 1420$^a$ | 2680$^a$ |

$^a$Averaged data from two tests
$^b$2-(3',5'-di-t-butyl-2'-hydroxyphenyl)-5-chlorobenzotriazole

We claim:

1. Compositions comprising (A) materials subject to ultraviolet light degradation and (B) from about 0.05 part to about 10 parts by weight per 100 parts by weight of the material of substituted decahydroquinoline compounds and the dimers thereof having the structural formula

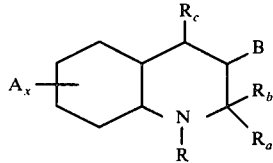

wherein R is selected from the group consisting of alkyl groups containing 1 to about 24 carbon atoms, aralkyl groups of 7 to about 14 carbon atoms, cyclohexylalkyl groups of 7 to about 14 carbon atoms total, hydroxyalkyl groups containing 1 to about 12 carbon atoms, haloalkyl groups containing 1 to about 12 carbon atoms, cyanoalkyl groups containing 2 to about 12 carbon atoms, aminoalkyl or iminoalkyl groups containing 2 to about 12 carbon atoms, ether groups containing 3 to about 18 carbon atoms total in the group, hydroxyalkylether or cyanoalkylether groups containing 4 to about 18 carbon atoms total in the group, and the group

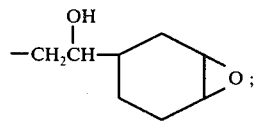

$R_a$, $R_b$, and $R_c$ each independently are alkyl groups containing 1 to about 12 carbon atoms, cyclohexyl groups, or cyclohexylalkyl groups containing 7 to about 14 carbon atoms; A is selected from the group consisting of alkyl groups containing 1 to about 24 carbon atoms, hydroxyalkyl groups containing 1 to about 12 carbon atoms, alkoxy groups containing 1 to about 12 carbon atoms in the group, ester groups containing a total of from 2 to about 24 carbon atoms in the group, a cyclohexyl group, cyclohexylalkyl groups containing 7 to about 14 carbon atoms in the group, a hydroxy group, amino groups and aminoalkyl groups and alkyl- substituted amino and aminoalkyl groups wherein the alkyl contains 1 to about 12 carbon atoms; x is 0, 1, 2, or 3; and B is hydrogen, an alkyl group containing 1 to about 12 carbon atoms, a cyclohexyl group, or a cyclohexylalkyl group of 7 to about 14 carbon atoms in the group; and, further, wherein the dimers of the above compounds are essentially two decahydroquinoline compounds of the above structural formula attached to each other at the 4-positions, the 6-positions, the 8-positions, the 4'-,6'-positions, and the 4'-,8-positions on the molecule.

2. A composition of claim 1 wherein (A) is a polymeric material.

3. A composition of claim 2 wherein (A) the polymeric material is a polyolefin polymer, and (B) is a substituted decahydroquinoline compound wherein R is an alkyl of 1 to about 18 carbon groups, benzyl, a hydroxyalkyl group of 1 to about 6 carbon atoms, a hydroxyalkyl ether group of 4 to about 12 carbon atoms, a cyanoalkyl group of 2 to about 6 carbon atoms, or an aminoalkyl group of 1 to about 6 carbon atoms; $R_a$, $R_b$, and $R_c$ are alkyl groups having 1 to about 12 carbon atoms; A is alkyl, alkoxy, cyclohexylalkyl, alkylamino, or aminoalkyl; x is 0, 1, or 2; and wherein B is hydrogen or an alkyl group having 1 to about 12 carbon atoms.

4. A composition of claim 3 wherein (A) is a poly-α-monoolefin homopolymer and (B) is a substituted decahydroquinoline compound wherein R is an alkyl group, a hydroxyalkyl group, cyanoalkyl group, or an aminoalkyl group; $R_a$, $R_b$ and $R_c$ are alkyl groups of 1 to about 6 carbon atoms; A is an alkyl group of 1 to about 10 carbon atoms; x is 0, 1, or 2; and B is hydrogen or a methyl or ethyl group.

5. A composition of claim 4 wherein (A) is polypropylene.

6. A composition of claim 5 wherein the substituted decahydroquinoline compound is selected from the group consisting of 1,2,2,4-tetramethyl decahydroquinoline, 1-decyl-2,2,4-trimethyl decahydroquinoline, 1-(2'-hydroxyethyl)-2,2,4-trimethyl decahydroquinoline, 1-(2'-hydroxyethyl)-2-methyl-2,4-diethyl decahydroquinoline, 1-(2'-hydroxyethyl)-2-methyl-2,4-dihexyl decahydroquinoline, 1-(2'-hydroxyethyl)-2,2,4,7-tetramethyl decahydroquinoline, 1-(2'-hydroxyethyl)-2,2,4,8-tetramethyl decahydroquinoline, 1-(2'-hydroxybutyl)-2,2,4-trimethyl decahydroquinoline, 1-(2'-cyanoethyl)-2,2,4-trimethyl decahydroquinline, 1-(3'-aminopropyl)-2,2,4-trimethyl decahydroquinoline, and 6-[4'-(1,2,2,4-tetramethyl decahydroquinolyl)]-1,2,2,4-tetramethyl decahydroquinoline.

7. A composition of claim 6 wherein the substituted decahydroquinoline compound is 1-(2'-hydroxyethyl)-2,2,4-trimethyl decahydroquinoline.

8. A composition of claim 1 where in (B) the decahydroquinoline compound is a bis compound wherein the bis compound is essentially two decahydroquinoline compounds of the structural formula in claim 1 attached to each other through the 1-positions, the 4-positions, the 6-positions, or the 8-positions via a bivalent radical structure selected from the group consisting of a bivalent alkyl structure and the structure $-(CH_2)_y-G-(CH_2)_z-$ wherein G is -O-, -S-, >NH,

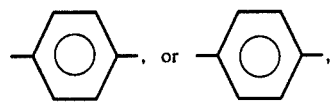

and $y$ and $z$ are individually an integer from 1 to 6.

9. A composition of claim 1 wherein the composition additionally contains antioxidants used in the range of from about 0.1 part to about 10 parts by weight per 100 parts by weight of the material.

10. A composition of claim 9 wherein the antioxidant is a phenolic antioxidant.

11. A composition of claim 10 wherein the phenolic antioxidants are those having alkylhydroxyphenyl substituents on an ester or a heterocyclic nucleus.

* * * * *